(12) United States Patent
Yi et al.

(10) Patent No.: US 7,604,817 B2
(45) Date of Patent: Oct. 20, 2009

(54) METHOD FOR PROMOTING GROWTH OF TISSUE

(75) Inventors: Chin-Feng Yi, Somerville, NJ (US); Anna Gosiewska, Skillman, NJ (US); Susan Roweton, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1423 days.

(21) Appl. No.: 10/654,145

(22) Filed: Sep. 3, 2003

(65) Prior Publication Data
US 2008/0131477 A1 Jun. 5, 2008

Related U.S. Application Data

(62) Division of application No. 09/832,700, filed on Apr. 11, 2001, now Pat. No. 6,656,488.

(51) Int. Cl.
A61F 2/00 (2006.01)
C12N 11/02 (2006.01)
C12N 11/08 (2006.01)
C12N 5/06 (2006.01)
C12N 5/08 (2006.01)

(52) U.S. Cl. ............... 424/423; 424/426; 424/93.7; 435/177; 435/180; 435/395

(58) Field of Classification Search .............. None
See application file for complete search history.

(56) References Cited

U.S. PATENT DOCUMENTS

| | | | |
|---|---|---|---|
| 3,811,133 A | 5/1974 | Harris | |
| 4,105,034 A | 8/1978 | Shalaby et al. | |
| 4,130,639 A | 12/1978 | Shalaby et al. | |
| 4,140,678 A | 2/1979 | Shalaby et al. | |
| 4,141,087 A | 2/1979 | Shalaby et al. | |
| 4,205,399 A | 6/1980 | Shalaby et al. | |
| 4,208,511 A | 6/1980 | Shalaby et al. | |
| 4,453,939 A | 6/1984 | Zimmerman et al. | |
| 4,664,662 A | 5/1987 | Webster | |
| 4,772,284 A | 9/1988 | Jefferies et al. | |
| 4,818,542 A | 4/1989 | DeLuca et al. | |
| 4,837,285 A | 6/1989 | Berg et al. | |
| 4,936,858 A | 6/1990 | O'Keefe | |
| 5,116,371 A | 5/1992 | Christensen et al. | |
| 5,411,554 A | 5/1995 | Scopelianos et al. | |
| 5,464,929 A | 11/1995 | Bezwada et al. | |
| 5,595,751 A | 1/1997 | Bezwada et al. | |
| 5,597,579 A | 1/1997 | Bezwada et al. | |
| 5,607,687 A | 3/1997 | Bezwada et al. | |
| 5,618,552 A | 4/1997 | Bezwada et al. | |
| 5,620,698 A | 4/1997 | Bezwada et al. | |
| 5,630,842 A | 5/1997 | Brodniewicz | |
| 5,632,774 A | 5/1997 | Babian | |
| 5,645,850 A | 7/1997 | Bezwada et al. | |
| 5,648,088 A | 7/1997 | Bezwada et al. | |
| 5,697,976 A | 12/1997 | Chesterfield et al. | |
| 5,698,213 A | 12/1997 | Jamiolkowski et al. | |
| 5,700,583 A | 12/1997 | Jamiolkowski et al. | |
| 5,716,404 A | 2/1998 | Vacanti et al. | |
| 5,770,193 A | 6/1998 | Vacanti et al. | |
| 5,859,150 A | 1/1999 | Jamiolkowski et al. | |
| 5,969,020 A | 10/1999 | Shalaby et al. | |
| 6,017,598 A | 1/2000 | Kreischer et al. | |

FOREIGN PATENT DOCUMENTS

| | | |
|---|---|---|
| EP | 0648480 | 4/1995 |
| GB | 2281861 | 3/1996 |
| WO | WO85/04413 | 10/1985 |
| WO | WO91/06286 | 5/1991 |
| WO | WO97/34645 | 9/1997 |
| WO | WO99/18886 | 4/1999 |
| WO | WO00/33771 | 6/2000 |

OTHER PUBLICATIONS

Kasper CS, Chandler PJ Jr, "Talc deposition in skin and tissues surrounding silicone gel containing prosthetic devices", Arch Dematol, Jan. 1994; 130(1): 48-53.
Barker DE, Retsky MI, Schultz S,. "bleeding" of silicone from baggel breast implants, and its clinical relation to fibrous capsule reaction, Plast Reconstr Surg. Jun. 1978;61(6): 836-41.
Rimaiex F,. Masson J, Couturaud B, Revol M, Servant JM, "Breast reconstruction by inflatable anatomical implant", Ann Chir Plast Esthet, Jun. 1999;44(3):239-45 (Infotrieve Abstract).
Raphael Gorodetsky et al. Fibrin Microbeads (FMB) as Biodegradable Carriers for culturing Cells and for Accelerating Wound Healing, 0022-202X/99 Copyright 1999 by The Society for Investigative Dermatology, Inc. pp. 866-872.
E. Bulgarelli et al. Effect of matrix composition and process conditions on casein-gelatin beads floating properties, International Journal of Pharmaceutics 198 (2000) 157-165.
K. Yoncheva et al,. "Development of biodegradable poly(a-methylmalate) microspheres", Pharmazie 55 (2000) pp. 148-150.
Y. Murata et al. Preparation of alginate gel beads containing chitosan nicontinic acid salt and the functions, European Journal of Phamaceutics and Biopharmaceutics 48 (1999) 49-52.
R. A. Jain et al.. "Controlled delivery of drugs from a novel injectable in situ form ed biodegradable PLGA microsphere system", J. Microencapsulation, 2000, vol. 17, No. 3, 343-362.
Plogmeir K et. al, "Breast reconstruction; autogulous tissue versus implant", Zentralable Chir 1998, 123 Suppl 5:100-2 (Infotrieve Abstract).
Burg et al., "Absorbable Mesh Aids in Development of Discrete, Tissue-Engineered Constructs", Critical Review in Biomedical Engineering, 28 (3 & 4):383:387, 2000 by Begell House, Inc., John R. Bourne and Yu V. Gulyaev, Editors.
Allcock, H.R. 'Polyphosphazenes' Encyclopedia of Polymer Science and Engineering. (1988) vol. 13, pp. 31-41. Wiley Intersciences, John Wiley & Sons.
Cohn, D., et al. 'Biodegradable PEO/PLA Block Copolymers' Journal of Biomedical Materials Research. (1988) vol. 22 pp. 993-1009.

(Continued)

Primary Examiner—David M Naff

(57) ABSTRACT

A device and method for tissue engineering is disclosed. More particularly this invention relates to a bioabsorbable device and a method of its use which promotes controlled new tissue in-growth into voids or cavities occupied by the device as portions of the device are selectively absorbed within a host thereby minimizing collapse of surrounding, pre-existing host tissue into the engineered site.

16 Claims, 1 Drawing Sheet

OTHER PUBLICATIONS

Cohn, D. 'New Tailor-Made Biodegradable Polymeric Biomaterials' Polymer Preprints (ACS Division of Polymer Chemistry) (1989) vol. 30(1) pp. 498.

Heller, J. 'Poly(Ortho Esters)' Handbook of Biodegradable Polymers. Edited by Domb, et al. (1997) pp. 99-118.

Kemnitzer, J., et al. 'Degradable Polymers Derived from the Amino Acid L-Tyrosine' Handbook of Biodegradable Polymers. Edited by Domb, et al. (1997) pp. 251-272.

Vandorpe, J. et al, 'Biodegradable Polyphosphazenes for Biomedical Applications' Handbook of Biodegradable Polymers edited by Domb, et al. (1997) pp. 161-182.

METHOD FOR PROMOTING GROWTH OF TISSUE

This application is a Divisional of application Ser. No. 09/832,700, now U.S. Pat. No. 6,656,488, filed on Apr. 11, 2001, titled 'Bioabsorbable Bag Containing Bioabsorbable Materials Of Different Bioabsorption Rates For Tissue Engineering,' which is hereby incorporated by reference.

BACKGROUND OF THE INVENTION

1. Field of the Invention

This invention is concerned with a device and method for tissue engineering. More particularly this invention relates to a bioabsorbable device and a method for promoting controlled new tissue in-growth into voids or cavities occupied by the device as portions of the device are selectively absorbed within a host thereby minimizing collapse of surrounding, pre-existing host tissue into the engineered site. The device and method are particularly well suited for soft tissue engineering applications such as breast reconstruction and the healing of wound cavities.

2. Related Art

In the area of reconstructive surgery, tissue engineering is one approach to correct defects caused through removal of cancerous cells or debridement of other malignant masses of cells. Breast reconstruction is important for patients who undergo surgical procedures due to breast cancer. Some of the options for breast reconstruction include insertion of permanent implants (prostheses) and autologous tissue flap techniques using the latissimus dorsi as a flap, transverse rectus abdominis musculocutaneous flap, or free flap. Some of the prosthetic implants include anatomic saline implants and silicone bag-gel implants. However, disadvantages have been reported for these types of implants; for example, anatomic saline implants have been reported as having the disadvantage of persistent rippling and difficulty of the choice of size (*Breast reconstruction by inflatable anatomical implant*. Ann Chir Plast Esthet, 1999 June; 44(3): 239-45) and silicone bag-gel breast implants have been associated with leakage of silicone gel, which causes fibrous thickening, and various degrees of inflammation (*"Bleeding" of Silicone from Bag-Gel Breast Implants, and its Clinical Relation to Fibrous Capsule Reaction*. Plast Reconstr Surg, 1978 June; 61(6): 836-41). Even without the leakage of the silicone gel, this type of implant can cause periprosthetic capsules and excessive capsular sclerosis (*Talc Deposition in Skin and Tissues Surrounding Silicone Gel-containing Prosthetic Devices*, Arch Dematol, 1994 January; 130(1):48-53). Autologous tissue flaps have been reported potentially leading to necrosis (*Breast Reconstruction: Autologous Tissue versus Implant*, Zentralble Chir 1998; 123 Suppl 5:110-2).

U.S. Pat. No. 5,716,404 discloses methods and compositions for reconstruction or augmentation of breast tissue. Dissociated cells, preferably muscle cells, are implanted in combination with a suitable biodegradable, polymeric matrix to form new tissue. Two types of matrices are disclosed: a polymeric hydrogel formed of material such as an alginate having cells suspended therein, and a fibrous matrix having an interstitial spacing of between about 100 and 300 microns. In a preferred embodiment, the cell matrix is implanted in conjunction with tissue expander devices. As the cell-matrix is implanted, or cells proliferate and form new tissue, the expander size is decreased, until it can be removed and the desired reconstruction or augmentation is obtained.

The present invention provides an advance over the prior art by providing a fully bioabsorbable device capable of setting to the desired shape and being replaced by controlled in-growth of host tissue as hereinafter described.

SUMMARY OF THE INVENTION

Figure 1:
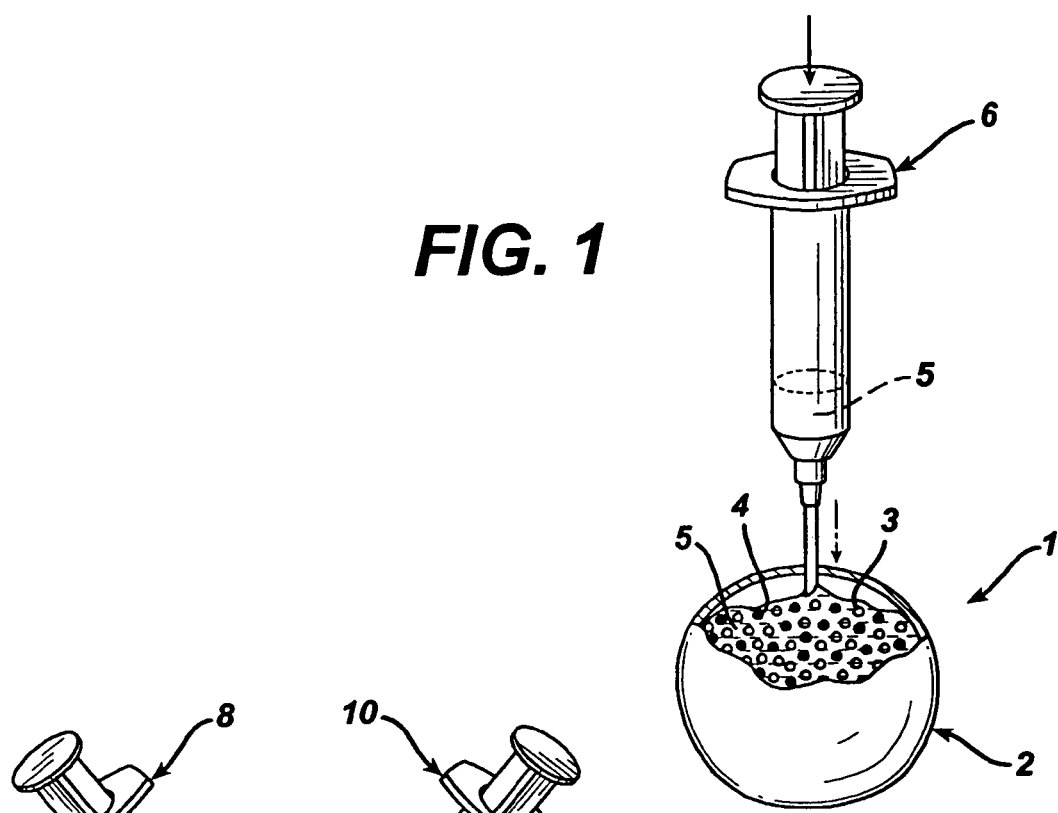
FIG. 1 depicts one embodiment for the device of the invention comprising a bioabsorbable bag containing fast-bioabsorbable and slow-bioabsorbable beads being injected with a bioabsorbable binding and setting gel.

One aspect of this invention relates to a device for tissue engineering comprising:
  a) a porous bioabsorbable bag;
  b) at least two bioabsorbable materials each material having a different rate of bioabsorption, the materials being of sufficient size so as to be contained within the porous bag; and
  c) a bioabsorbable binding gel which sets and binds the bioabsorbable materials in relation to each other.

Another aspect of the invention relates to a method for promoting in-growth of host tissue into a void within the host comprising the steps of:
  a) providing a porous bioabsorbable bag comprising at least two bioabsorbable materials, each material having a different rate of bioabsorption and each material of sufficient size so as to be contained in the bag;
  b) injecting into the bag a bioabsorbable binding gel capable of binding and setting the bioabsorbable materials in relation to each other; and
  c) inserting the bag of step b into the void and conforming the bag to the desired shape within the void.

In an alternate embodiment, the invention relates to a method for promoting in-growth of host tissue into a void within the host comprising the steps of:
  a) providing a porous bioabsorbable bag comprising at least two bioabsorbable materials, each material having a different rate of bioabsorption and each material of sufficient size so as to be contained in the bag;
  b) inserting the bag of step a into the void and conforming the bag to the desired shape within the void; and
  c) injecting into the bag a bioabsorbable binding gel capable of binding and setting the bioabsorbable materials in relation to each other and further conforming the bag to the desired shape within the void.

Advantages of this invention include being a fully bioabsorbable device that permits controlled in-growth of host tissue. When the device is fully absorbed, the space that the device occupied is now filled with the host's own tissue. The device is also capable of quickly setting to the desired shape alleviating the necessity of having to continually reduce the size of the tissue expanders associated with other methods. In addition, the presence of autologous plasma concentrate or fibrin gel might provide nutrients and stimulants for cells either migrating into or present within the device.

DETAILED DESCRIPTION OF PREFERRED EMBODIMENTS OF THE INVENTION

One aspect of this invention relates to a device for tissue engineering comprising:
  a) a porous bioabsorbable bag;
  b) at least two bioabsorbable materials each material having a different rate of bioabsorption, the materials being of sufficient size so as to be contained within the porous bag; and c) a bioabsorbable binding gel which sets and binds the bioabsorbable materials in relation to each other.

As used herein, the term bioabsorbable is intended to describe materials that will degrade in the host through hydrolysis and further absorb in vivo; i.e. materials which are eliminated from the host through natural pathways either because of simple filtration of degradation by-products or after their metabolization. The term "bag" as used herein is intended to include any type of container suitable for use with the invention as herein described.

The size of the pores of the bioabsorbable bag should be large enough to permit passage of cells into the bag but small enough to prevent the bioabsorbable material contents of the bag from spilling out of the bag. Suitable pore sizes range from approximately 30-100 micrometers (μm) in diameter which allows cell and bodily fluid migration into the bag as typical cell sizes are in the range of 5-20 μm. While any suitable degree of porosity may be used for the bag, a porosity of approximately 50% porosity is envisaged as suitable for most applications.

The shape of the bioabsorbable bag may be any shape needed to fulfill the required application and should be conformable to the size and shape of the intended application (e.g., breast reconstruction, wound cavity filling, etc.) The conformability feature of the bioabsorbable bag is discussed in more detail below in conjunction with the discussion of the binding and setting of the bioabsorbable materials.

The porous bioabsorbable bag may be made from a porous sheet of a bioabsorbable material or made from woven or non-woven bioabsorbable materials. One way to make the porous sheet (membrane) of bioabsorbable material for the bioabsorbable bag is described in Example 1. It will be appreciated by one skilled in the art that the reported pore size of the porous membrane is easily manipulated by controlling the crystal size of the salt use during the manufacture of the membrane.

Regarding the woven or non-woven forms of the bioabsorbable bag, these may be comprised of any bioabsorbable biocompatible material in embodiments including textiles with woven, knitted, warped knitted (i.e., lace-like), non-woven, and braided structures. In an exemplary embodiment, the porous membrane has a mesh-like structure. In any of the above structures, mechanical properties of the material can be altered by changing the density or texture of the material, or by embedding particles in the material. As described more fully below, the materials used to make the fibers for the above forms of the bioabsorbable bags may comprise any biocompatible material including bioabsorbable materials such as polylactic acid (PLA), polyglycolic acid (PGA), polycaprolactone (PCL), polydioxanone (PDO), trimethylene carbonate (TMC), polyvinyl alcohol (PVA), copolymers, or blends thereof.

Thus in the mesh form of the porous bag of this invention, the bag may comprise an organized network selected from the group consisting of threads, yarns, nets, laces, felts, and non-wovens. A preferred mesh product is VICRYL (TRADEMARK) mesh manufactured by Ethicon Inc. Pore sizes in the mesh may reach as high as 400 to 600 μm, but typically average approximately 200 μm.

The bioabsorbable fibers used to prepare the porous bags according to the present invention may be solid or hollow, or may be of a sheath/core construction. Filaments may be co-extruded to produce a sheath/core construction. Additionally, such constructs may be formed by coating a bioabsorbable fiber, e.g., a bioabsorbable glass fiber, with a bioabsorbable polymer. Methods for making each construct of filament are well known to those skilled in the art. In a co-extruded construction, each filament comprises a sheath of biodegradable polymer that surrounds one or more cores comprising another bioabsorbable polymer. Filaments with a fast-absorbing sheath surrounding a slow-absorbing core may be desirable in instances where extended support is necessary for tissue in-growth.

The bioabsorbable bag and the bioabsorbable materials that are placed in the bioabsorbable bag may comprise any number of known bioabsorbable materials provided that there are at least two bioabsorbable materials of differing bioabsorption rates that are placed in the bag. That is to say that one of the bioabsorbable materials placed in the bag degrades faster than the other. It is envisaged for most applications that the fast degrading bioabsorbable material degrade approximately in 7-14 days and is that the slow degrading beads begin degrading after approximately 7-14 days and be completely degraded in approximately 30-60 days. Regarding the rate of absorption of the bioabsorbable bag, it is envisioned that the bag will have a rate of bioabsorption at least as long as the rate of bioabsorption as the slow bioabsorbing material. Of course it is within the level of skill in the art for one to optimize the relative absorption rates of the bioabsorbable materials placed in the bag and the rate of absorption of the bioabsorbable bag itself to best promote in-growth of new tissue. Such factors to consider in making this determination include condition of the host, the rate or ability that the host is able to produce the necessary cells for in-growth, and the use of any cell growth promoters in conjunction with the device.

A variety of bioabsorbable polymers can be used to make the porous bag and slow-absorbing and fast-absorbing materials of the present invention. These bioabsorbable polymers include both synthetic polymers such as polyesters and biopolymers such as polypeptides, polysaccharides and derivatives thereof. Examples of suitable biocompatible, bioabsorbable polymers include but are not limited to polymers selected from the group consisting of aliphatic polyesters, poly(amino acids), copoly(ether-esters), polyalkylenes oxalates, polyamides, polyacetals, polyketals, polycarbonates, polyorthocarbonates, polyurethanes, poly(alkylene succinates), poly(maleic acid), poly(methyl vinyl ether), poly(maleic anhydride)tyrosine derived polycarbonates, poly(iminocarbonates), polyorthoesters, polyoxaesters, polyamidoesters, polyoxaesters containing amine groups, poly(anhydrides), polyphosphazenes, bioploymers (e.g., collagen, gelatin, alginate, pectin, starch, fibrin, oxidized cellulose, chitin, chitosan, tropoelastin, hyaluronic acid and mixtures thereof) and mixtures thereof. For the purpose of this invention aliphatic polyesters include, but are not limited to, homopolymers and copolymers of lactide (which includes lactic acid, D-,L- and meso lactide), glycolide (including glycolic acid), ε-caprolactone, p-dioxanone (1,4-dioxan-2-one), trimethylene carbonate (1,3-dioxan-2-one), alkyl derivatives of trimethylene carbonate, δ-valerolactone, β-butyrolactone, γ-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, 2,5-diketomorpholine, pivalolactone, γ,γ-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one and polymer blends thereof. Poly(iminocarbonates), for the purpose of this invention, are understood to include those polymers as described by Kemnitzer and Kohn, in the *Handbook of Biodegradable Polymers*, edited by Domb, et. al., Hardwood Academic Press, pp. 251-272 (1997). Copoly(ether-esters), for the purpose of this invention, are understood to include those copolyester-ethers as described in the Journal of Biomaterials Research, Vol. 22, pages 993-1009, 1988 by Cohn and Younes, and in Polymer Preprints (ACS Division of Polymer Chemistry), Vol. 30(1), page 498, 1989 by Cohn (e.g. PEO/PLA). Polyalkylene oxalates, for the purpose of this invention, include those described in U.S. Pat. Nos. 4,208,511; 4,141,087; 4,130,639; 4,140,678; 4,105,034; and 4,205,399. Polyphosphazenes, co-, ter- and higher order mixed monomer-based polymers made from L-lactide, D,L-lactide, lactic acid, glycolide, glycolic acid, para-dioxanone, trimethylene carbonate and ε-caprolactone such as are described by Allcock in *The Encyclopedia of Polymer Science*, Vol. 13, pages 31-41, Wiley Intersciences, John Wiley & Sons, 1988 and by Vandorpe, et al in the *Handbook of Biodegradable Polymers*, edited by Domb, et al, Hardwood Academic Press, pp. 161-182 (1997). Polyanhydrides include those derived from diacids of the form HOOC—$C_6H_4$—O—$(CH_2)_m$—O—$C_6H_4$—COOH, where m is an integer in the range of from 2 to 8, and copolymers thereof with aliphatic alpha-omega diacids of up to 12 carbons. Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150. Polyorthoesters such as those described by Heller in *Handbook of Biodegradable Polymers*, edited by Domb, et al, Hardwood Academic Press, pp. 99-118 (1997).

Poly(L-lactide) ("PLA"), poly(d,l-lactide) ("PDLA"), poly(glycolide) ("PGA"), polycaprolactone, copolymers, terpolymer, higher poly-monomer polymers thereof, or combinations or mixtures thereof are preferred biocompatible, bioabsorbable polymers. PLA, PDLA, PGA, and combinations or mixtures or blends thereof are among the synthetic polymers approved for human clinical use. They are presently utilized as surgical suture materials and in controlled release devices, as well as in other medical and pharmaceutical applications. They are biocompatible and their degradation products are low molecular weight compounds, such as lactic acid and glycolic acid, which enter into normal metabolic pathways. Furthermore, control of the composition of poly(lactic-co-glycolic acid) copolymers facilitates control of the degradation profile.

The preferred bioabsorbable materials for the bioabsorbable bag construction are poly(ε-caprolactone) ("PCL") and poly(glycolide) (PGA). The co-monomer ratios are preferably between about 0:100 to about 50:50 ε-caprolactone to glycolide. Most preferably, the co-monomer ratios are about 30:70 to about 50:50 ε-caprolactone to glycolide.

The preferred bioabsorbable copolymers for the slow degrading bead construction are poly(L-lactide) ("PLA") and poly(glycolide) ("PGA"). The co-monomer ratios are preferably between about 100:0 to about 0:100 L-lactide and glycolide. Most preferably, the monomer ratios are about 85:15 L-lactide and glycolide.

Preferred materials for the fast degrading bioabsorbable materials include collagen, gelatin, alginate, pectin, starch, fibrin, oxidized cellulose, chitin, chitosan, tropoelastin and hyaluronic acid and mixtures thereof.

To enhance biodegradation of the polymers used in biological applications, the compositions of the present invention can also include the addition of enzymes that can facilitate the biodegradation of the polymers used in the composition.

Preferred enzymes or similar reagents are proteases or hydrolases with ester-hydrolyzing capabilities. Such enzymes include, without limitation, proteinase K, bromelaine, pronase E, cellulase, dextranase, elastase, plasmin streptokinase, trypsin, chymotrypsin, papain, chymopapain, collagenase, subtilisn, chlostridopeptidase A, ficin, carboxypeptidase A, pectinase, pectinesterase, an oxidoreductase, an oxidase or the like. The inclusion of an appropriate amount of such a degradation-enhancing agent can be used to regulate implant duration.

Immune suppressor agents that can be incorporated in the bag and bead constructions, include, without limitation, corticosteroids and anti-metabolites such as 5-fluoro-uracil or any other immune suppressor agents or agents that interfere.

It will be appreciated by those skilled in the art that many variations are possible for acceptable fast or slow degrading materials and the bioabsorbable bag. In fact, in the case of PLA/PGA copolymers, as noted above, the relative ratios of the materials used to produce the copolymers may be varied to achieve varying rates of bioabsorbability. Therefore, it is possible to have both the fast and slow degrading beads made of PLA/PGA copolymers with differing ratios of PLA and PGA. Crosslinking may also be used as a variable to control the rate of bioabsorption for a material of the same composition; for example, one skilled in the art may use collagen as both the fast and slow bioabsorption material with the slow-absorbing collagen more highly crosslinked than the fast-absorbing collagen.

The bioabsorbable, materials placed in the bioabsorbable bag may be of any shape suitable for conformation in the desired application including, but not limited to, fibers, beads, pellets, granules, powders, flakes and the like. A preferred shape for the bioabsorbable material is that of spherical beads or pellets, which provide the ability to easily be shaped for filling the desired sites that may be of irregular shape. Typical sizes for the bead or pellet form of the bioabsorbable materials have diameters ranging from 100 to 1000 micrometers. Of course, the selection of bead diameter would be sized sufficiently so as to remain within the porous bag. Thus, when the pores of the bioabsorbable bag are 100 micrometers, the size of the bead or pellet diameters would be greater than 100 micrometers.

Gels suitable for use in this invention encompass any bioabsorbable gel capable of binding and setting the bioabsorbable materials in relation to each other. Suitable gels include both synthetic and biological gels.

As used herein, the terms binding and setting are intended to mean that the gel is capable of restricting the relative degree of motion between the bioabsorbable materials contained within the bag to an extent wherein the gel and bioabsorbable material-containing bag are capable of being conformed or shaped into the desired form suitable for the particular application. Thus, once the gel is applied and begins to bind and set the bioabsorbable materials within the bag, the consistency of the materials in the bag permit molding and facilitate shape retention before becoming permanently set.

Examples of suitable synthetic gels include hydrogels such as polyphosphazenes, poly vinyl alcohols (PVA), polyethylene oxides (PEO), pluronic polyols, polyacrylates, and mixtures thereof.

Examples of suitable biological gels include but are not limited to fibrin or autologous plasma concentrates which form gel upon mixing with thrombin, any extracellular matrix proteins, including collagen, laminin, elastin and proteoglycans which form gels either upon mixing with crosslinking agents or changing physical environment such as pH and temperature.

Although not required as part of the invention, wound healing stimulants may be added to the contents of the bioabsorbable bag to help promote the infusion of cells into the bag to promote new tissue growth. In some embodiments it may be desirable to add bioactive molecules to the cells. A variety of bioactive molecules can be delivered using the bioabsorbable materials described herein. These are referred to generically herein as "factors" or "bioactive factors".

Suitable bioactive factors are growth factors, angiogenic factors, compounds selectively inhibiting in-growth of fibroblast tissue such as anti-inflammatories, and compounds selectively inhibiting growth and proliferation of transformed (cancerous) cells. These factors may be utilized to control the growth and function of infiltrated cells, implanted cells, the in-growth of blood vessels into the forming tissue, and/or the deposition and organization of fibrous tissue around the bioabsorbable bag.

Examples of suitable growth factors include heparin binding growth factor ("HBGF"), platelet-derived growth factor ("PDGF"), transforming growth factor alpha or beta ("TGF-α" or "TGF-β"), basic fibroblast growth factor ("bFGF"), epidermal growth factor ("EGF"), vascular endothelial growth factor ("VEGF"), some of which are also angiogenic factors. Other factors include hormones such as insulin, glucagon, and estrogen. In some embodiments it may be desirable to incorporate factors such as nerve growth factor ("NGF") or muscle morphogenic factor ("MMP").

Where selective chemotherapeutic agents are available which do not inhibit growth of normal cells, such as antibody-targeted chemotherapeutic agents, these can be incorporated into the bioabsorbable bag and used to inhibit any residual cancer cells remaining following a surgical procedure.

These factors are known to those skilled in the art and are available commercially or described in the literature. In vivo dosages may be calculated based on in vitro release studies in cell culture; an effective dosage is that dosage which increases cell proliferation or survival as compared with controls. Preferably, the bioactive factors are incorporated to between one and 30% by weight, although the factors can be incorporated to a weight percentage ranging between 0.01 and 95 weight percentage.

Bioactive molecules can be incorporated into the bioabsorbable bag device and released over time by diffusion and/or degradation of the device, they can be suspended with any cell suspension used in conjunction with the device, they can be incorporated into bioabsorbable materials such as beads which are suspended with the cells or attached to or incorporated within the device, or some combination thereof. Release properties can also be determined by the size and physical characteristics of the bioabsorbable materials used.

Although not required as part of the invention, cells may be added to the contents of the bioabsorbable bag to help speed the healing process. Suitable cells include, but are not limited to stem cells and autologous cells obtained from other parts of the body. One example of cells could be a mixture of various cell types derived from liposuction.

One embodiment of the method of this invention comprises a method for promoting in-growth of host tissue into a void within the host comprising the steps of:
  a) providing a porous bioabsorbable bag comprising at least two bioabsorbable materials, each material having a different rate of bioabsorption and each material of sufficient size so as to be contained in the bag;
  b) injecting into the bag a bioabsorbable binding gel capable of binding and setting the bioabsorbable materials in relation to each other; and
  c) inserting the bag of step b into the void and conforming the bag to the desired shape within the void.

The method of use of the device for promoting in-growth of host tissue can be accomplished by a user mixing the gel, the bioabsorbable materials and optional wound healing stimulants and/or cells together by rubbing the bag from the outside.

In an alternate embodiment, the invention relates to a method for promoting in-growth of host tissue into a void within the host comprising the steps of:
  a) providing a porous bioabsorbable bag comprising at least two bioabsorbable materials, each material having a different rate of bioabsorption and each material of sufficient size so as to be contained in the bag;
  b) inserting the bag of step a into the void and conforming the bag to the desired shape within the void; and
  c) injecting into the bag a bioabsorbable binding gel capable of binding and setting the bioabsorbable materials in relation to each other and further conforming the bag to the desired shape within the void.

Figure 2:
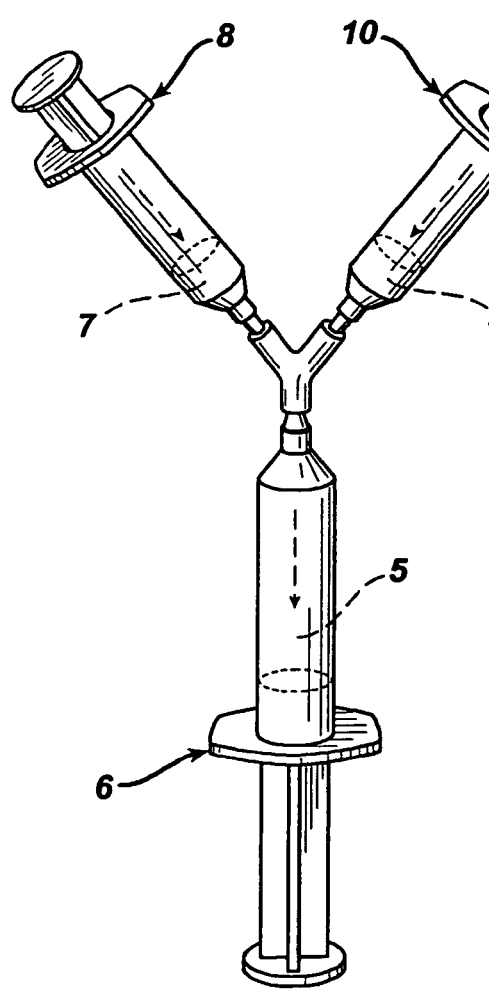
FIG. 2 depicts an embodiment wherein the mixing of two components comprising the bioabsorbable binding and setting gel are combined together into an injection device.

Referring to FIG. 1, one embodiment of the device (1) of this invention is depicted to comprise a bioabsorbable bag (2); fast-absorbing beads (3); slow-absorbing beads (4); and the bioabsorbable binding and setting gel (5) being injected into the device (1) by means of an injector (6). FIG. 2 shows an embodiment wherein, the binding and setting gel (5) of injector (6) is comprised of two components for example plasma concentrate or fibrogen (7) contained in injector (8) and thrombin (9) contained in injector (10). Of course, other components of the gel are suitable for use as well as use of optional wound healing stimulants and/or cells that can be injected into device (1) either separately or together with the gel (5).

If certain shapes are required for a particular application, the bag may be placed in a mold before the gel solidifies. In the case wherein the gel comprises thrombin, the time required for solidification depends on the amount of thrombin added to the gel. The bag is then ready to be placed in the cavity. At this point, fluid can enter into the scaffold of the device and the fast degrading beads can begin to degrade. The presence of nutrients and wound healing stimulants in the fibrin or autologous plasma concentrate may enhance the host cell migration, proliferation and extracellular matrix synthesis and deposition within the bag. The degradation of the fast bioabsorbable beads provides space for cell migration and proliferation (includes cells from surrounding tissue or from optionally added autologous or allogenic cells). At a later time, for example, greater than 14 days, the slow bioabsorbable beads degrade and more space is available for cell migration, proliferation and extracellular matrix deposition. At the final stage, the biodegradable bag may be replaced with the new tissue.

The following examples are illustrative of some of the ways of making the devices of this invention.

EXAMPLE 1

Membrane construction for bioabsorbable bag: PCL/PGA (35/65) copolymer was dissolved in 1,4-dioxane to obtain a 5% (wt/wt) solution. Sodium chloride crystals were ground using a coffee grinder and then sieved so that particles with a diameter ranging from 75 to 106 μm were obtained. The sieved sodium chloride crystals (10 grams) were mixed in 9 ml PCL/PGA (35/65) solution. This mixture was cast onto 8" Teflon coated dish and dried in a fume hood for 24 hours. To leech the salt crystals from the membrane, the membrane was washed with approximately one gallon of water per day, for three days. The membrane was then dried in a desiccator under low vacuum for 24 hours. Pores were formed in the membrane from the use of the sodium crystals resulting in pore sizes ranging from approximately 72-103 μm as measured using light microscopy and image analysis.

Slow-degrading bead construction: PLA/PGA (85/15) copolymer was dissolved in 1,4-dioxane to obtain a final 5% (wt/wt) solution. The beads were made using the Pronova Coaxial Bead Generator (Oslo, Norway). The polymer solution was fed into the bead generator using a peristaltic pump. By varying the pump flow rate and air pressure on the bead generator unit, beads between the size of 400 to 1000 μm were made. The beads were collected in liquid nitrogen and were lyophilized. This process generated porous beads.

Fast-degrading bead construction: Gelatin (Bloom 175) was dissolved in water to obtain a 5% (wt/wt) solution. The rest of the bead making procedure was the same as for the slow-degrading beads, as mentioned above. To crosslink the lyophilized beads, acetone-water 3:1 (v/v) containing 0.5% glutaraldehyde was mixed with beads at 1:1 volume ratio for 6 hours at 5° C. The cross-linked beads were washed with an excess of cold acetone (5° C.) at approximately 10 times volume of the bead's volume and dried in a desiccator under low vacuum.

Bag construction: Two pieces of membrane (above), were cut into circles approximately 4 cm in diameter and were superimposed to form a bag. The edges of both pieces were sealed with a hot wire (100° C.). An opening at one portion of the bag was formed and the bag was subsequently filled with slow and fast-degrading beads at a ratio of 1:1.

Fibrin gel preparation: Bovine fibrinogen and thrombin were mixed together to obtain a final concentration of 30 mg/ml and 5 units/ml, respectively. The mixture was injected into the bead-containing bag. The setting of the gel took place approximately within 5 minutes. The bag opening was closed with a bioabsorbable suture.

EXAMPLE 2

A second bag was constructed in a similar manner to that described in EXAMPLE 1 except that the bioabsorbable material used for the bag was VICRYL (TRADEMARK) copolymer of glycolic acid and lactic acid (90:10) mesh manufactured by Ethicon Inc. under the tradename of POLYGLACTIN 910. The pore size formed by the mesh was measured to average approximately 200 μm.

It should be understood that the foregoing disclosure and description of the present invention are illustrative and explanatory thereof and various changes in the size, shape, and material composition, as well as in the description of the preferred embodiment, may be made without departing from the spirit of the invention.

What is claimed is:

1. A method for promoting in-growth of host tissue into a void within the host comprising the steps of:
    a) providing a porous bioabsorbable bag comprising at least two bioabsorbable materials, each material having a different rate of bioabsorption and each material of sufficient size so as to be contained in the bag;
    b) injecting into the bag a bioabsorbable binding gel capable of binding and setting the bioabsorbable materials in relation to each other; and
    c) inserting the bag of step b into the void and conforming the bag to the desired shape within the void, whereby in-growth of host tissue into the void is promoted.

2. A method for promoting in-growth of host tissue into a void within the host comprising the steps of:
    a) providing a porous bioabsorbable bag comprising at least two bioabsorbable materials, each material having a different rate of bioabsorption and each material of sufficient size so as to be contained in the bag;
    b) inserting the bag of step a into the void and conforming the bag to the desired shape within the void; and
    c) injecting into the bag a bioabsorbable binding gel capable of binding and setting the bioabsorbable materials in relation to each other and further conforming the bag to the desired shape within the void, whereby in-growth of host tissue into the void is promoted.

3. The method of claims 1 or 2, wherein the porous bioabsorbable bag and the bioabsorbable materials are made from the group consisting of polyesters and biopolymers.

4. The method of claim 3, wherein the size of the pores of the porous bag range from 30 to 600 micrometers.

5. The method of claim 3, wherein the bioresorbable bag and the bioresorbable materials are selected from the group consisting of aliphatic polyesters, poly(amino acids), copoly (ether-esters), polyalkylenes oxalates, polyamides, polyacetals, polyketals, polycarbonates, polyorthocarbonates, polyurethanes, poly(alkylene succinates), poly(maleic acid), poly (methyl vinyl ether), poly(maleic anhydride), tyrosine derived polycarbonates, poly(iminocarbonates), polyorthoesters, polyoxaesters, polyamidoesters, polyoxaesters containing amine groups, poly(anhydrides), polyphosphazenes, polypeptides, polysaccharides, polysaccharide derivatives and mixtures thereof.

6. The method of claim 5, wherein the shape of the bioabsorbable materials is selected from the group consisting of fibers, beads, pellets, granules, powders, flakes and combinations thereof.

7. The method of claim 6, wherein the bioabsorbable materials are in the form of beads and range in size from 100 to 1000 micrometers.

8. The method of claim 6, wherein the gel is selected from the group consisting of hydrogels, fibrin or autologous plasma mixed with thrombin, extracellular matrix proteins, proteoglycans, and mixtures thereof 9. The method of claim 8, wherein the extracellular matrix proteins are selected from the group consisting of collagen, laminin, elastin, and mixtures thereof.

10. The method of claim 9, wherein the bioabsorbable bag comprises copolymers of poly(L-lactide) and poly (glycolide) in a ratio range about 100:0 to about 0:100 of L-lactide to glycolide or copolymers of poly(ε-caprolactone) and poly (glycolide) in a ratio range of about 0:100 to about 50:50 ε-caprolactone to glycolide, one of the bioabsorbable materials comprises copolymers of poly(L-lactide) and poly (glycolide) in a ratio range of about 100:0 to about 50:50 of L-lactide to glycolide, the other of the bioabsorbable materials comprises a material selected from the group consisting of collagen, gelatin, alginate, pectin, starch, fibrin, oxidized cellulose, chitin, chitosan, tropoelastin hyaluronic acid and mixtures thereof, and the binding gel comprises fibrin or autologous plasma mixed with thrombin.

11. The method of claim 10, wherein the bag comprises pores in the range of about 30 to 600 micrometers, the bioabsorbable materials comprise beads in the range of 100 to 1000 micrometers.

12. The method of claim 1 or 2, wherein the host tissue is soft tissue.

13. The method of claim 1 or 2, wherein the void within the host tissue is a wound cavity.

14. The method of claim 1 or 2, wherein the host tissue containing the void is breast tissue.

15. The method of claim 1 or 2, wherein the host tissue containing the void is bone tissue.

16. The method of claim 1 further comprising the step of placing the bag from step b into a mold and forming a molded shape before beginning step c.

* * * * *

UNITED STATES PATENT AND TRADEMARK OFFICE
CERTIFICATE OF CORRECTION

PATENT NO. : 7,604,817 B2  Page 1 of 1
APPLICATION NO. : 10/654145
DATED : October 20, 2009
INVENTOR(S) : Yi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1802 days.

Signed and Sealed this

Fifth Day of October, 2010

David J. Kappos
*Director of the United States Patent and Trademark Office*